United States Patent

Berta

Patent Number: 5,679,406
Date of Patent: Oct. 21, 1997

[54] TABLET DIPPING SYSTEMS FOR APPARATUS FOR GELATIN COATING TABLETS

[75] Inventor: Norbert I. Berta, Devon, Pa.

[73] Assignee: McNeil-PPC, Inc., Skillman, N.J.

[21] Appl. No.: 462,241

[22] Filed: Jun. 5, 1995

Related U.S. Application Data

[60] Division of Ser. No. 3,158, Jan. 12, 1993, Pat. No. 5,503,673, which is a continuation-in-part of Ser. No. 609,482, Nov. 5, 1990, Pat. No. 5,228,916.

[51] Int. Cl.$^6$ .................. B05D 1/18; B05D 1/32; B05D 3/12
[52] U.S. Cl. .................. 427/289; 427/2.14; 427/294; 427/296; 427/430.1
[58] Field of Search .................. 427/2.18, 2.14, 427/2.22, 2.23, 289, 296, 430.1, 294; 118/423

[56] References Cited

U.S. PATENT DOCUMENTS

| | | | |
|---|---|---|---|
| 499,542 | 6/1893 | Heineman | 427/212 |
| 3,453,989 | 7/1969 | Bippus | |
| 4,510,168 | 4/1985 | Sakashita et al. | 427/2.14 |
| 4,526,129 | 7/1985 | Braden | 118/503 |
| 4,597,931 | 7/1986 | Watanabe et al. | 118/421 |
| 4,669,416 | 6/1987 | Delgado et al. | 118/503 |
| 4,684,113 | 8/1987 | Douglas et al. | 269/21 |
| 4,694,776 | 9/1987 | Sandbach et al. | 269/56 |
| 4,820,524 | 4/1989 | Berta | 424/474 |
| 4,867,983 | 9/1989 | Berta | 424/451 |
| 4,921,108 | 5/1990 | Berta | 209/625 |
| 4,940,499 | 7/1990 | Lebrun et al. | 118/24 |
| 4,965,089 | 10/1990 | Sauter et al. | 427/2.22 |
| 4,966,771 | 10/1990 | Berta | 424/478 |
| 4,990,358 | 2/1991 | Berta | 427/2.22 |
| 5,098,749 | 3/1992 | Gabriel et al. | 427/430.1 |
| 5,228,916 | 7/1993 | Berta | 118/30 |
| 5,234,099 | 8/1993 | Berta | 198/803.1 |
| 5,314,537 | 5/1994 | Berta | 118/30 |
| 5,436,026 | 7/1995 | Berta | 427/2.14 |
| 5,466,290 | 11/1995 | Berta | 427/2.14 |
| 5,498,441 | 3/1996 | Berta | 427/2.14 |
| 5,503,673 | 4/1996 | Berta | 427/2.14 |

FOREIGN PATENT DOCUMENTS

| | | |
|---|---|---|
| 271627 A | 6/1988 | European Pat. Off. |
| 0448231A1 | 9/1991 | European Pat. Off. |
| 127081 | 10/1928 | Switzerland ............ 269/21 |

*Primary Examiner*—Diana Dudash

[57] ABSTRACT

An apparatus and method for dipping products, such as tablets, into coating material and for spreading and setting the coating immediately after dipping is provided. Carrier plates having a plurality of tablet holders are transported from a tablet loading station to a dipping station along a transport guide. At the dipping station, a carrier plate is mounted to a vacuum chamber. A set of vacuum tubes in the vacuum chamber are extended through the tablet holders to contact and lift the tablets off of the holders and secure the tablets to the tubes. In a preferred embodiment, the vacuum chamber is rotated 180° and a second carrier plate is mounted onto the housing and a second set of tubes secure the tablets to the plate. The carrier plates are alternately dipped and returned to the guide means where new plates with uncoated tablets replace the plates with coated tablets. Immediately after dipping the carrier plates enter a rotating station where the plate is rotated 360° and then replaced on the guide means for transportation to further processing stations. Preferably, the rotating station includes a similar vacuum chamber with vacuum tubes that are extended into the holder for securing the tablet during rotation.

1 Claim, 15 Drawing Sheets

TABLET DIPPING SYSTEMS FOR APPARATUS FOR GELATIN COATING TABLETS

This is a division of application Ser. No. 08/003,158, filed Jan. 12, 1993, now U.S. Pat. No. 5,503,673, which is a continuation-in-part application of application Ser. No. 07/609,482, filed Nov. 5, 1990, now U.S. Pat. No. 5,228,916, all of which are hereby incorporated by reference.

The present invention relates to methods and apparatus for forming a coating on a product and, more particularly, to methods and apparatus for forming a coating comprised of a gelatinous substance on a tablet. The present invention further relates to methods and apparatus for dipping tablets into the coating material.

The present invention is related to my prior patents U.S. Pat. Nos. 4,921,108 issued on May 1, 1990; 4,867,983 issued on Sep. 19, 1989; 4,820,524 issued on Apr. 11, 1989 and 4,966,771 issued on Oct. 30, 1990, and my U.S. Patent Application 483,154, filed Feb. 22, 1990, now U.S. Pat. No. 5,234,099 which are assigned to the assignee of the present application and incorporated by reference as if fully set forth herein.

The present invention is also related to my U.S. Patent Applications, Serial Nos. 08/003,334, now abandoned, 08/003,347, now U.S. Pat. No. 5,466,290; 08/003,348, now U.S. Pat. No. 5,436,026; and 08/003,349, now U.S. Pat. No. 5,498,411 all filed concurrently herewith, which are all assigned to the assignee of the present application and incorporated by reference as if fully set forth herein. These related applications disclose methods and apparatus suitable for forming gelatinous coatings on tablets.

BACKGROUND OF THE INVENTION

Many products, from prescription drugs to commonly available vitamin tablets to candy, are manufactured in a form which may be described as a "tablet." The primary function of a tablet is to provide a single dose or "serving" of the product in a manner which is convenient to manufacture, package and consume. As pointed out in my previous patents and applications, referenced above, it has been found that to certain individuals suffer from physiological and psychological problems which impede their ability to swallow tablets. It has also been found that by providing tablets with a smooth coating, such as a coating comprised of gelatin or a gelatinous substance that the "swallowability" of a tablet is greatly enhanced. Such coatings and the general considerations involved in their application, such as preparation and drying time, are well known to those of ordinary skill.

In addition to enhanced swallowability, there are numerous other reasons that it is desirable to provide a coating on a tablet. Such coatings protect the underlying product from deterioration and also serve to permit identifying colors or markings to be incorporated onto the design of the product, promoting product differentiation and brand identification. As pointed out in my previous patents and applications, it is also desirable in some instances to overlap two or more coatings to form a seam, thereby simulating the appearance of a hard gelatin capsule while providing a coated, solid (and thus tamper resistant) product. Methods and apparatus for applying a gelatinous coating or other coating to a product which is in the form of a tablet are well known to those of ordinary skill. Such methods may include pan dipping or vacuum spraying of the coating material on to the tablet. Such methods are crude, however, producing uneven coatings which are generally unacceptable for commercial use.

In an effort to improve the state of the art, the inventions disclosed by my previous patents and applications have provided methods and apparatus whereby individual products are held partially within a sleeve or "collet" and the exposed portion of the product precisely lowered into a dipping tank. As disclosed, bars or plates containing a plurality of product to be dipped are conveyed and rotated and the product itself is manipulated to provide even coatings of high quality and consistency at high volume. These inventions, however, do not permit every type of product such as certain styles of tablets and medicaments to be coated—or at least to be coated in a particular manner. For example, dipping the circular face of a substantially cylindrical tablet whose height is relatively small compared to its diameter would be difficult using the apparatus disclosed by my prior patents and applications, particularly if a circumferential seam is desired. Other examples include the difficulty of coating either a fragile product or applying fragile coating compositions. It has been found that certain coatings will be marred by the friction fit within the collets or similar retaining devices making these unsuitable for use in the apparatus of my prior inventions.

It is known to transport individual tablets or capsules through an immersion coating bath by retaining the tablets on individual vacuum tubes. For example, U.S. Pat. No. 3,896,762—Banker discloses a rotary coating apparatus for pharmaceutical solid dosage forms. Since the surface of the coating is horizontal it is tangential to the path of the tablet; accordingly, Banker discloses that it is necessary to rotate the vacuum tube holding the tablet around its longitudinal axis to achieve an even coating. There are, however, a number of practical shortcomings in the apparatus disclosed. First, although a dryer and ejector are disclosed, the overall system does not lend itself to high volume production or provide for modifications in drying time or inspection, etc. Secondly, the system disclosed by Banker is directed to passing one-half or more of the total depth dimension of the tablet through the coating solution. The tablet is then randomly ejected, with no provision being made to align or otherwise control the orientation of the tablet and the uncoated portion, if any, which exists. Moreover, there is no provision for adjusting the coating to achieve multi-colored or capsule-like coated products. Therefore, one of ordinary skill will appreciate that the system disclosed by Banker is of limited use in current manufacturing environments, where high volume and flexibility are important, along with the need for consistency and high quality.

Therefore, there exists a need for methods and apparatus which can consistently place a precisely defined amount of coating material on an individual product. Such methods and apparatus should be capable of producing coated products at high volume and should possess inherent flexibility to permit new designs and types of coatings to be incorporated without an undue degree of retooling. Moreover, it is extremely important that the products be immersed into the coating material in a highly controlled manner to enable the coatings to be of high quality and consistency.

SUMMARY OF THE INVENTION

The present invention is directed to an apparatus for dipping tablets into a gelatin coating material and for spreading and setting the coating immediately after dipping. Carrier plates having a plurality of tablet holders are transported from a tablet loading station to a dipping station along a transport guide means. At the dipping station, a carrier plate is grabbed from the guide means and mounted to a vacuum chamber means. A first set of vacuum tubes in the vacuum chamber means are actuated to extend the tubes through the tablet holders to contact and lift the tablets off of the holders. A vacuum source is activated to secure the tablets to the tubes. In a preferred embodiment, the vacuum chamber means is rotated 180° and a second carrier plate is mounted onto the chamber means. A second set of tubes are extended and activated to secure the tablets to the second plate. The carrier plates mounted to the chamber means are alternately dipped and returned to the guide means to provide a high volume apparatus for continuously dipping tablets and transporting the tablets for further processing. The apparatus of the present invention operates by lowering the vacuum chamber means to immerse tablets into a tank containing gelatin, raising and rotating the chamber means 180°, returning the plate with coated tablets to the guide means, mounting the next plate from the loading station onto the chamber means, dipping the second plate into the gelatin and proceeding thereafter in a like manner.

Immediately after tablet dipping, the carrier plate enters a rotating station for spreading and setting the coating. The carrier plate is rotated 360° and then transported to further processing stations along the guide means. Preferably, the rotating station includes a similar vacuum chamber means with vacuum tubes that are extended into the holders for securing the tablets during rotation. In an alternative embodiment, the vacuum chamber means at the rotating station includes a resilient gasket member providing a fluid connection between the holders and the vacuum source wherein the vacuum holds the tablets into the holder seat during rotation.

Also disclosed is a power cut-off feature in which the dip tank is lowered in the event of power being shut so that tablets in the tank at the time of the shut off will not remain in the gelatin an extended period. If the tablets remain in the tank an extended period of time an uneven coating will result. The system includes a cam operated spring mechansim that maintains the tank in a raised position during the dipping process. When power is turned off, the spring is released lowering the tank sufficiently clear of tablets.

DETAILED DESCRIPTION OF THE PREFERRED EMBODIMENTS

Figure 1:
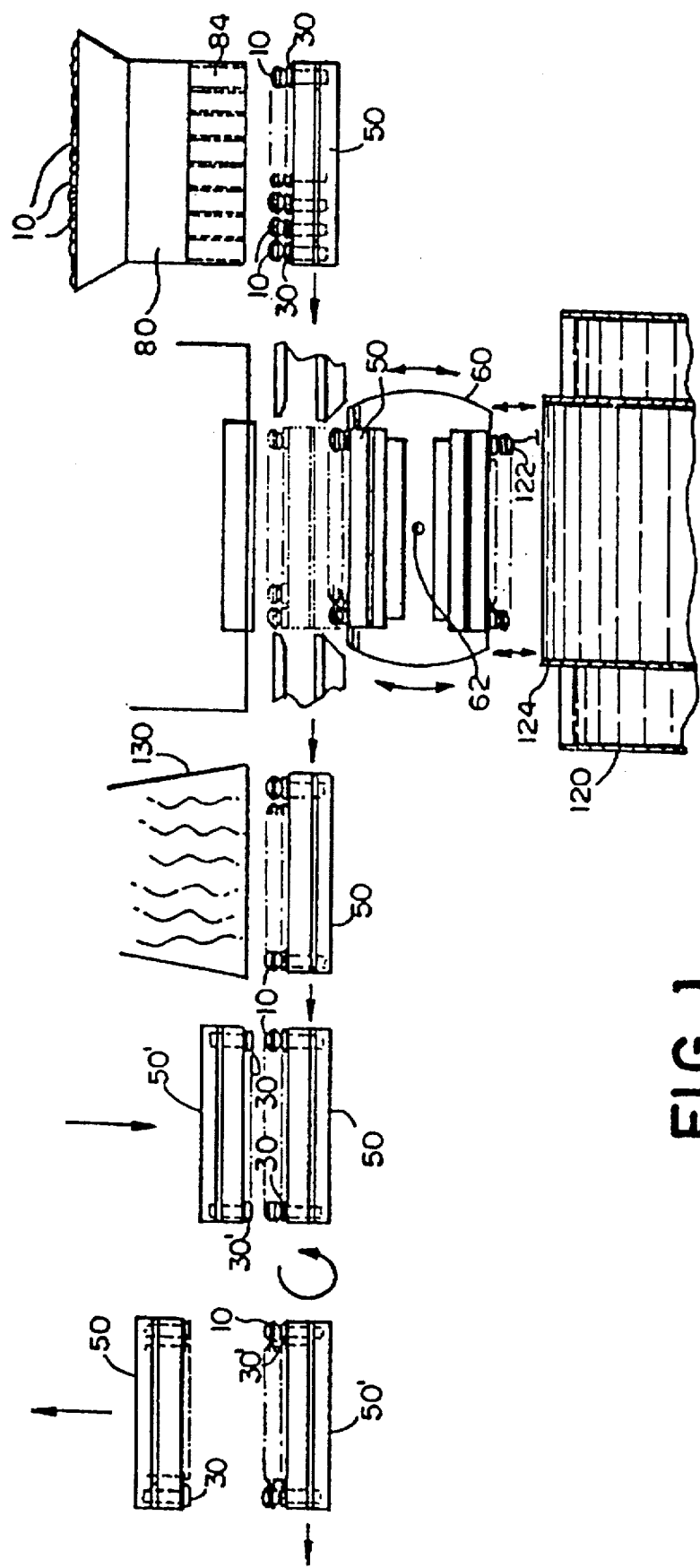
FIG. 1 is a partially diagrammatic, partially schematic representation of the coating apparatus of the present invention.

A generalized representation of the apparatus used in a preferred embodiment of the present invention is shown in FIG. 1. It will be understood that the descriptions set forth may be applied to numerous types and shapes of products. The type of tablet illustrated and the sequence shown are for purposes of explanation only.

A plurality of the product 10 to be coated is placed in a feeder means 80. Preferably, the feeder will be comprised of a hopper 82 and a series of feeder tubes 84 which align, orient and dispense the product 10 in the appropriate manner. Initially disposed directly beneath the feeder tubes 84 and in registration therewith is a plate 50. The plate 50 has a plurality of tablet holders 30 which, as explained below, restrain the product during certain portions of the coating process. The tablet holders 30 preferably correspond to the feeder tubes 84 and thus, most preferably, each tube 84 feeds a single product 10 into a single tablet holder 30.

Conveyor means transfer the plate 50 from the feeder 80 to the vacuum chamber 60. In a preferred embodiment shown in FIG. 1, the vacuum chamber 60 is adapted to receive and make vacuum tight connections with two plates 50. As shown by the arrows, the vacuum chamber 60 is further provided with manipulating means whereby it may be moved up and down, and rotated about a pivot point 62.

A first dipping tank 120 is disposed beneath the vacuum chamber 60 and is filled with a quantity of coating material. Preferably a coating material such as gelatin is used and, most preferably, the dipping tank 120 is provided with pumps and conduits whereby the coating material is continuously circulated. As illustrated, the dipping tank is most preferably constructed to form a meniscus surface 122 by pumping the coating material into an inner tank 124 which is permitted to overflow into the larger tank 120. Such a system prevents the coating material from hardening while the apparatus is in use and helps to ensure that the coating material presents the same even and substantially level surface to the product being dipped at all times.

In operation, the plate 50 is moved into engagement with the vacuum chamber 60 and then the chamber 60 and the plate 50 are rotated one-half revolution. As explained below, the vacuum chamber 60 creates a vacuum within the tablet holders 30 which holds the product 10 in place and in the correct orientation to be dipped. The vacuum chamber 60 is next lowered into dip tank 120 to a predetermined depth and then withdrawn. The vacuum chamber 60 is then rotated one and one-half revolutions in order to return the plate 50 to its original orientation. The additional full revolution beyond that required provides a dwell time, permitting the coating to initially "set" and also prevents the coating from running or sagging due to gravity by constantly reorienting the product 10. However, a rotation of as little as one-half of a revolution may be adequate in some instances. At this point, the plate 50 may be returned to the conveyor means and removed from the vacuum chamber 60.

In an alternative embodiment, a separate rotating station is provided adjacent the dipping station. In this embodiment, the dip station vacuum chamber rotates one-half revolution to return the plate to the conveyor. The plate is then transferred to a second vacuum chamber which engages the plate and rotates one revolution to provide the setting and spreading of the gelatin. The plate is then released and transferred to further processing stations.

The design of the vacuum chamber 60 and placement of the dip tank 120 illustrated permit a wide variety of coatings to be effectively and efficiently achieved. Although the dipping of a substantially cylindrical tablet having concave faces to form a coating having circumferential seam is illustrated, those of ordinary skill will understand that numerous other shapes of product, as well as other coating schemes are possible using the apparatus disclosed. As will be explained below, the shape of the tablet holders 30 and the design of the sub-components of the vacuum chamber 60 may be readily adapted for particular requirements. Also, as illustrated in FIG. 1, throughput may be increased by designing the vacuum chamber 60 to form a vacuum tight seal with further plates 50, such that each time the vacuum chamber 60 is rotated, a plate 50 which has already been lowered into the dipping tank 120 is returned to the conveyor means.

After the plate 50 containing the partially coated product 10 is removed from the vacuum chamber 60 the plate may be passed through a dryer means 130 for curing the coating material. As will be understood by those of ordinary skill, the dryer 130 will be chosen to correspond to the heat and moisture requirements of the coating material being used. Radiant heat, forced hot air, microwave dryers and combinations of these types are among the types available. Depending upon the type of dryer 130 chosen, one or more conveyors and other apparatus may be required to transfer the plates 50 into and out of the dryer 130.

After the coating has been cured, the plate 50 is again returned to conveyor means and is preferably transferred to another location. At this point, although only a portion of each individual product 10 has been coated, it may be desirable to eject the product 10 and consider the process complete. This may be true, for example, where the product has already been coated and the above-described process is carried out to add a second color to a portion of the product.

In a preferred embodiment, however, the present invention provides methods and apparatus which permit the uncoated portion of the product 10 to be coated. First, a second plate 50' is positioned in registration with the product contained on the first plate 50, as illustrated in FIG. 1. The second plate 50' is lowered until the coated side of the product 10 is disposed within the tablet holders 30' of the second plate 50'. The resulting "sandwich" of the first plate 50, the product 10 and the second plate 50' is then rotated one-half revolution by the conveyor/manipulator means. As shown, the positions of the plates 50,50' are thus reversed, and when the first plate 50 is removed the uncoated portion of the product 10 is exposed. The second plate 50' may then be transferred to the starting point of the dipping process and put through the sequence of manipulations necessary to form a coating which were set forth above using either the same apparatus or further apparatus, using either the same coating material or a different coating material.

In the instance where the same apparatus is used to place coating upon the uncoated portion of the product 10, the second plate 50' may be preferably conveyed or otherwise transported to a location just before the vacuum chamber 60, i.e., between the vacuum chamber 60 and the feeder 80 illustrated in FIG. 1. The second plate 50' would simply be inserted into engagement with the vacuum chamber 60 and the above described apparatus would carry out substantially the same sequence of functions in terms of dipping the product 10, curing the coating as needed, etc. After the product 10 has been fully coated and cured, it may be ejected prior to the transfer stage between the first and second plates 50,50'.

In another embodiment of the present invention, after the partially coated product has been transferred to the second plate 50', the plate 50' may enter a duplicate series of apparatus, such as that described above with reference to FIG. 1. In other words, a second vacuum chamber, dipping tank, dryer, and manipulating and conveying apparatus may be provided. After the product 10 is coated and cured using this second set of apparatus, the completed product is ejected.

Figure 2:
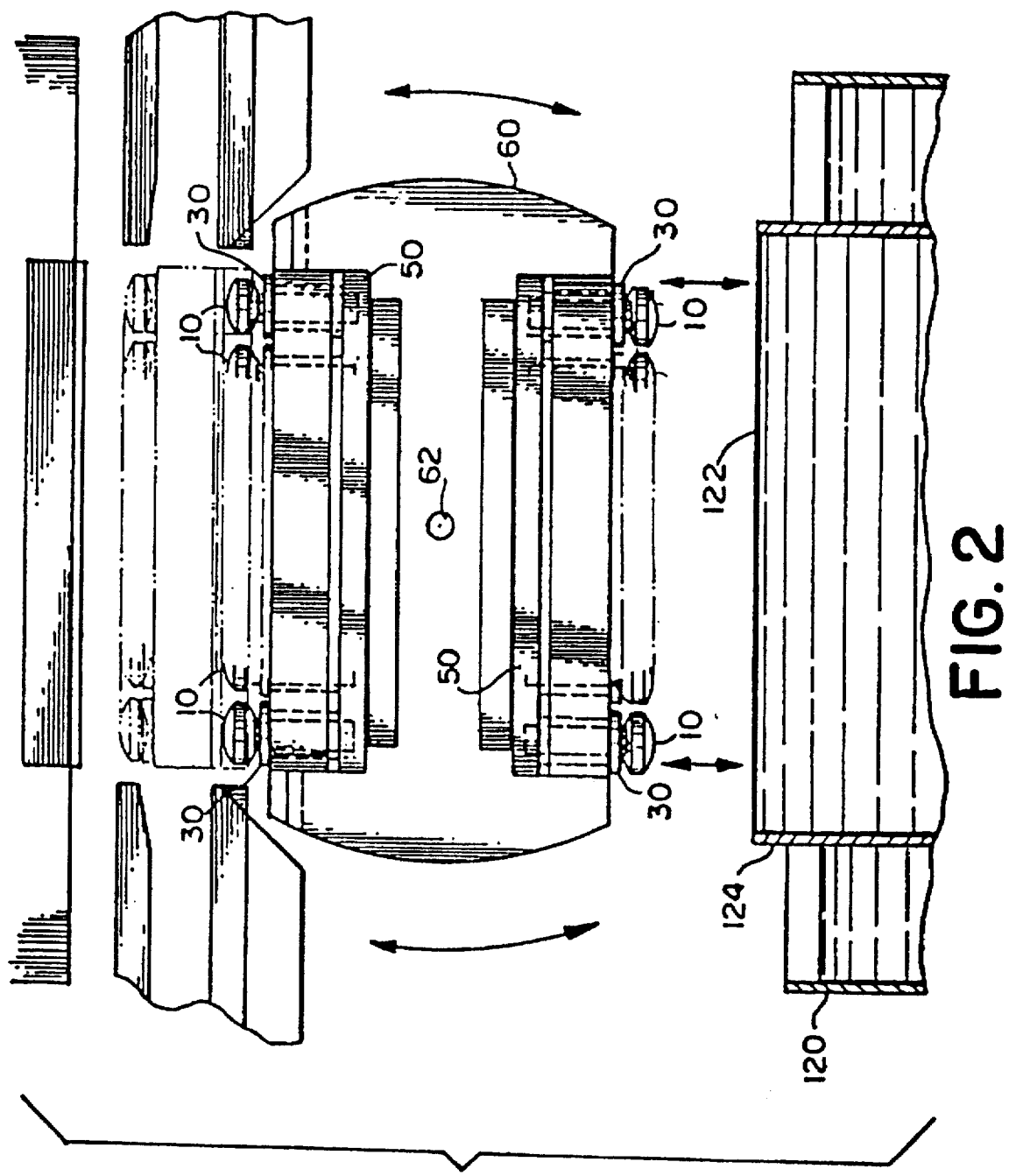
FIG. 2 is a broken away, partially cross-sectioned side view of a portion of the apparatus of FIG. 1.

Referring now to FIG. 2, a more detailed view of the vacuum chamber 60 described above is shown. As explained above, in a preferred embodiment two plates 50 (or 50') are retained in a vacuum tight seal upon the vacuum chamber 60, thereby permitting more efficient indexing between the raising and lowering of the apparatus and the infeed and outfeed of the plates 50 from the vacuum chamber 60.

As shown, the entire chamber may be raised or lowered to bring the product 10 into contact with the surface of the coating material 122. The vertical motion also preferably provides a transfer between the vacuum chamber 60 and the conveyor means, as shown in phantom in FIG. 2. This latter vertical movement also provides clearance when the vacuum chamber 60 is rotated during the dipping process explained above with reference to FIG. 1.

Figure 3:
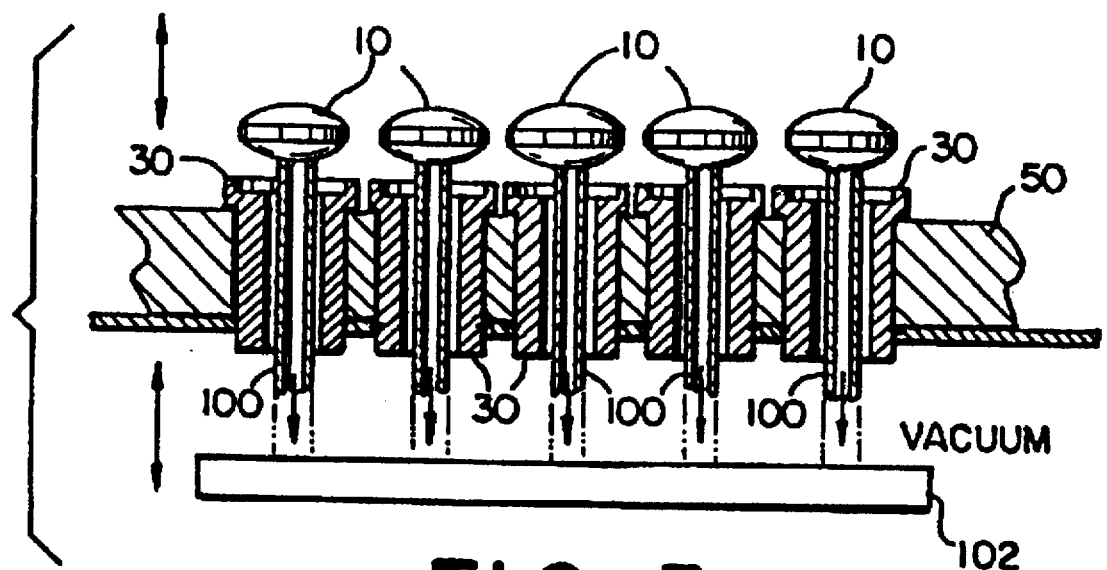
FIG. 3 depicts a cross-sectional view of the tablet holders and plate used in one embodiment of the present invention.

Further details of the vacuum chamber 60 are shown in FIG. 3, which illustrates broken-away section of the plate 50 and the vacuum chamber 60. As seen in cross-section, the plate 50 has a plurality of tablet holders 30 inserted into a series of openings. The plate 50 rests upon the vacuum chamber 60 and forms a seal therewith. A plurality of vacuum tubes 100 extend through the tablet holders 30 and, when in use, engage and slightly lift the product 10 from the tablet holders 30 as shown. The vacuum created within the vacuum chamber 60 is channeled through the vacuum tubes 100 by a manifold or similar means, thereby permitting the vacuum to act upon the surface of the product 10 when contacted by the vacuum tubes 100. By providing vacuum tube actuator means 102 for raising and lowering the vacuum tubes 100 relative to the vacuum chamber 60, the vacuum tubes may be selectively placed in the raised position illustrated. The actuator 102 may be a common bar or mounting structure which is moved by a gear, cam or pulley system.

When in the position illustrated, it is possible to invert or otherwise manipulate the product 10 as described above without friction or the use or mechanically actuated clamps. The vacuum handling system disclosed by the present invention provides a secure retention of the product while minimizing the possibility of damaging either the coating or the product 10 itself. As explained above, the methods and apparatus of the present invention are useful for numerous shapes and sizes of product 10, however, most preferably, the product 10 will have one or more curved surfaces, as illustrated. The curved surfaces permit the tubes 100 to be made from a rigid material such as stainless steel. Those of ordinary skill will realize however, that nearly any shape and any orientation of product may be retained using appropriately designed vacuum tubes. Finally, in certain instances it will be desirable to provide a cushion or resilient tip on the distal end of the vacuum tube in order to ensure a sufficient grip.

Figure 4:
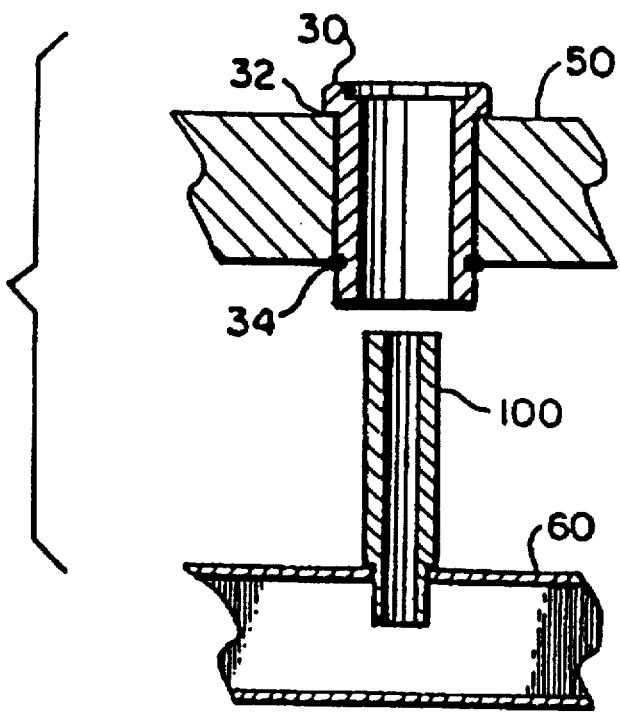
FIG. 4 is a broken away cross-sectional view of the plate of FIG. 3, illustrating the tablet holder and vacuum tube used in one embodiment of the present invention.

Referring now to FIG. 4, one embodiment of the tablet holder 30 is illustrated. A shoulder 32 is formed at a first end of the tablet holder to provide a positive stop. A groove is formed at a second end, into which an "O" ring or the like may be engaged to retain the tablet holder 30 in the plate 50. As will be understood by those of ordinary skill, the tablet holder 30 and the plate 50 may be in certain instances formed as an integral component. FIG. 4 also illustrates the vacuum tube 100 in the withdrawn position. When the vacuum tube 100 is in the withdrawn position, the depression formed in the tablet holder 30 is the only means for restraining the product 10 (not shown in FIG. 4).

Figure 7A:
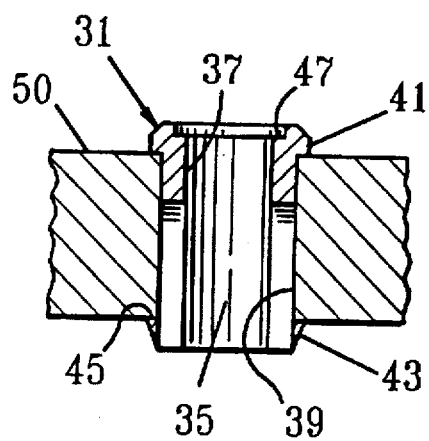
FIGS. 7a and 7b are cross-sectional views of another embodiment of a tablet holder of the present invention.
Figure 7B:
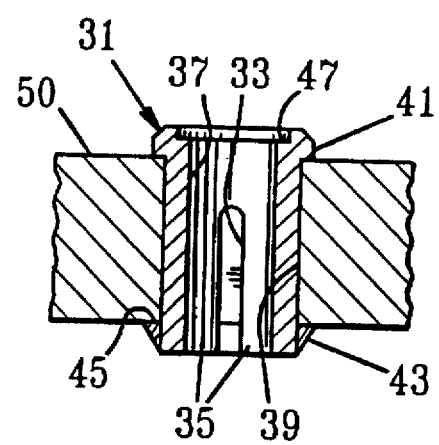

FIGS. 7a and 7b show a second embodiment of the tablet holder for use in plates 50. Tablet holder 31 shown in FIGS. 7a and 7b is provided with a plurality of slots 33 forming resilient fingers 35. FIG. 7a is a cross-section taken through the slots 33, and FIG. 7b is a cross-section taken with the holder 31 rotated 90° from its position in FIG. 7a. In the embodiment shown in FIGS. 7a and 7b, a pair of slots 33 are provided thereby forming a pair of resilient fingers 35. Slots 33 are disposed longitudinally through the walls of holder 31. Holder 31 is generally in the form of a cylinder having a central bore 37. Tablet holder 31 is retained in the opening 39 of plate 50 by shoulder portion 41 on one end and angled flange 43 on a second end. For ease in installation the size of upper surface 45 of angled flange 43 may be significantly reduced at the portion of the side walls located immediately adjacent to slots 33 as shown in FIG. 7a. The flange 43 may gradually increase to its largest surface area located 90° from slots 33 as shown in FIG. 7b. The holder 31 is also provided with seat 47 for accepting a tablet therein. It will be understood by those of ordinary skill that the seat 45 may be shaped appropriately to match the shape of the product being held.

The holder 31 is a "push-in" holder that does not require o-rings or the like that are susceptible to wear and tear. In order for the holder 31 to be secured in the plate 50, the outer diameter of the annular resilient fingers 35 forming the cylinder of holder 31 must be slightly larger than the diameter of the opening 39 in plate 50. The angle of flange 43 enables the holder 31 to be inserted through the opening 39 and to cause the fingers 35 to be slightly compressed toward each other as the holder is passed through the plate 50. When the flange 43 clears the opening 39 and plate 50, the resilient fingers 35 spring back to their original position causing flange 43 to engage plate 50 thereby securing the holder 31 therein.

Figure 8:
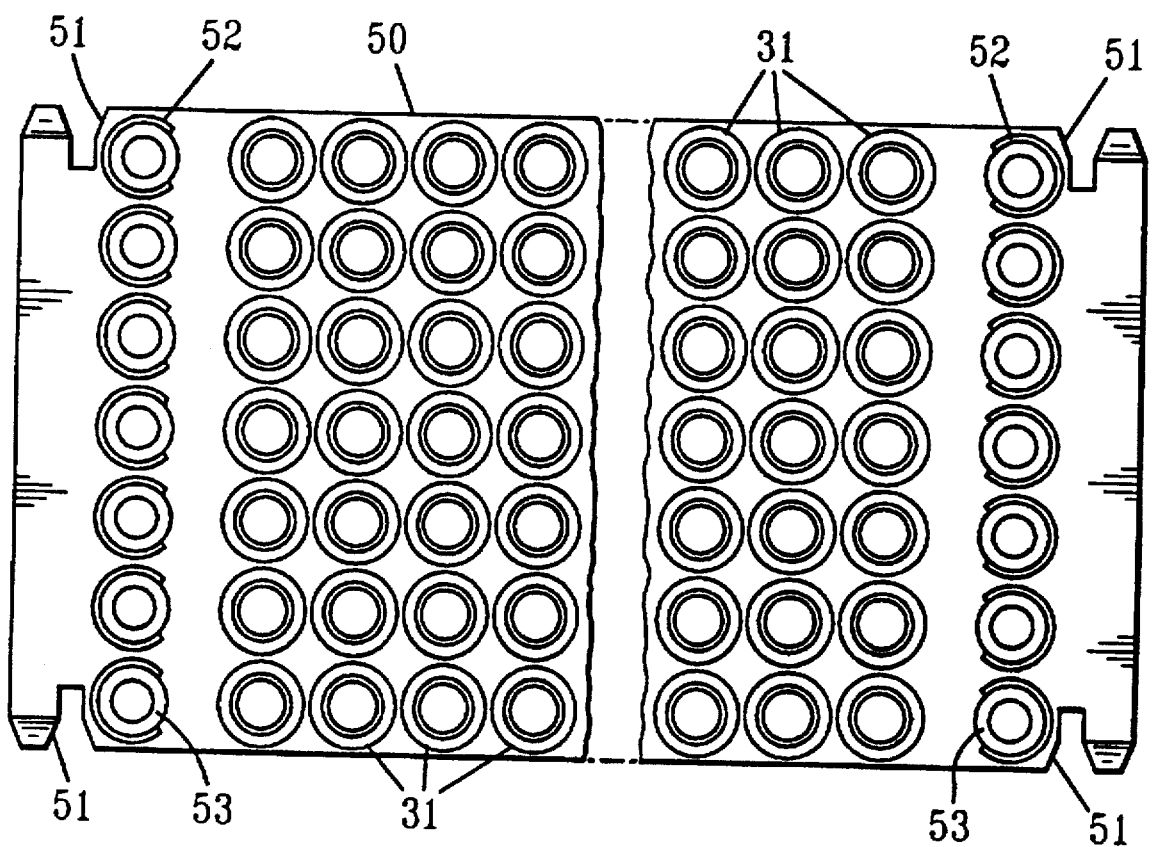
FIG. 8 is a plan view of a product carrier plate of one embodiment of the present invention.

FIG. 8 shows a plan view of a carrier plate 50 for retaining the plurality of product holders 30 or 31. The carrier plate 50 of FIG. 8 includes a plurality of longitudinal rows of individual product holders 31. The plates 50 are preferably from 4 to 5 inches wide and approximately one-half to one inch thick. In one embodiment, the plate 50 is made about 23 to 24 inches in length enabling the plate to include 7 rows each containing 33 holders for a total of 231 holders.

A preferred embodiment of the carrier plate 50 of the present invention is machined from tool plate aluminum. It is also preferred that the aluminum have a protective coating such as an anodized coating applied to the surface. The plate 50 is rectangular and symmetrical, having four easily spaced slots 51 disposed near the four corners which engage the conveyor and/or holding means. Also provided at either end are alignment and transport holes 52 which contain retaining bushings 53 which are used to manipulate the plate 50 as it is advanced through the feeder means 80 and through other processing stations.

The present invention also provides methods for coating a product 10 in accordance with the present invention. A preferred embodiment of the methods of the present invention is illustrated by the sequence of views in FIG. 5. For purposes of illustration and explanation a single product 10, vacuum tube 100 and tablet holder 30 are illustrated, along with broken away portions of other apparatus such as the plate 50. As shown in the upper left section of FIG. 1, a plate 50 containing a tablet holder 30 is positioned beneath the feeder means 80 for feeding a tablet described above and a product 10 is disposed within the tablet holder 30. Next, the plate 50 containing the individual products 10 is moved into the vicinity of the vacuum chamber 60, where it is cleaned of dust and particulate matter. For clarity, the representation of the vacuum chamber 60 is omitted from the other views shown in FIG. 5. An individual vacuum tube 100 is then brought into position and placed in close proximity or contact with the product 10. At this point, the vacuum created within the vacuum tube 100 "picks up" or engages the product 10. After the individual products 10 have been engaged by the vacuum tubes 100, the entire plate 50 is rotated one-half of a revolution, suspending the product 10 by the vacuum tube 100. The vacuum tube 100 and the product 10 attached thereto may now be moved into position and lowered into a coating tank 120. The depth to which the product 10 is lowered is a function of the motion of the vacuum tubes 100 and plate 50, which may be precisely regulated by hydraulic actuators, gear trains or other means for actuating the vacuum tube 100 and/or moving the plate 50. The vacuum tube 100 and the partially coated product 10 are then withdrawn from the coating tank 120, but the product 10 is not fully withdrawn into its holder 30. Instead, the plate 50 and partially extended vacuum tubes 100 are rotated one and one-half revolutions, returning the plate 50 to its initial orientation. Alternatively, the dipping vacuum chamber is rotated one-half revolution and the plate is then transferred to an adjacent second vacuum chamber that rotates the plate one revolution. The additional revolution provides a dwell, permitting the coating to initially set, as well as aiding in the provided evenness of the coating by preventing the coating from running due to gravity. In certain embodiments, however, this dwell may be unnecessary and the plate need only be rotated one-half of a revolution. After the plate 50 has been returned to its initial position, the vacuum tube 100 may be withdrawn until the product 10 again rests in a holder 30 within the plate 50. Once the vacuum tube 100 has been sufficiently withdrawn, the vacuum connection to the product 10 is broken and gravity and the holder 30 restrain the product 10.

Figure 5:
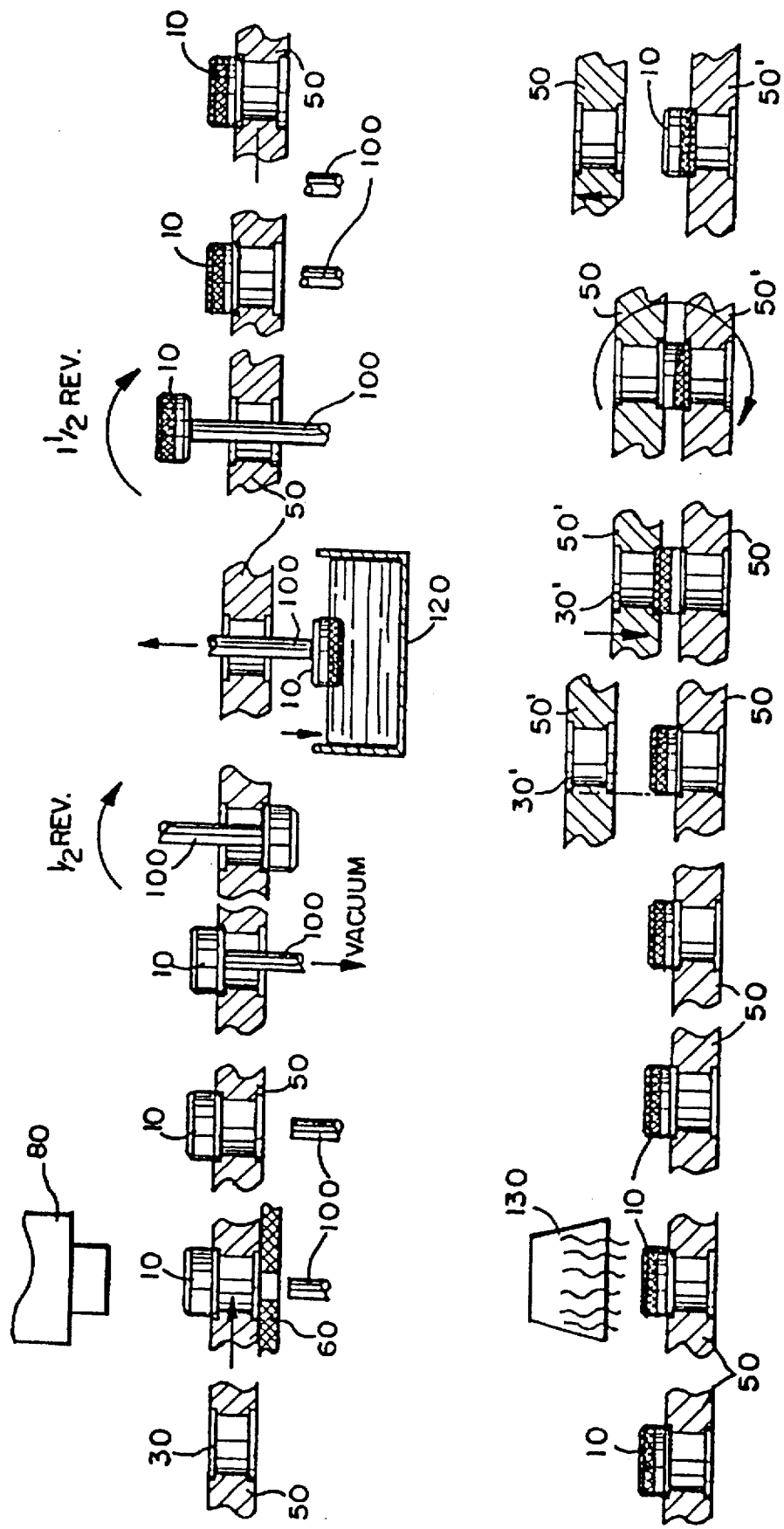
FIG. 5 is a partially diagrammatic, partially schematic representation of the steps of a preferred method for coating a tablet in accordance with the present invention.

As shown at the lower left portion of FIG. 5, once the individual products 10 have been released from the effect of the vacuum, the plate 50 bearing the partially coated individual products 10 may be moved into a dryer 130. Using conveyors or other conventional means, the plates are pushed into the dryer 130 and dried. After the coating has cured and the plates 50 have exited the dryer 130, a second plate 50' is moved into position such that the tablet holders 30' in the second plate 50' are in registry with the tablet holders 30 in the first plate 50, which contain the partially coated product 10. The second plate 50' is lowered toward the first plate 50 until the tablet holders 30' in the second plate 50' have engaged the product held in the first plate 50. Thus, as illustrated, the product 10 is "sandwiched" between the first and second plates 50,50'. The pair of plates 50,50' are then rotated one-half revolution, thereby reversing the relative positions of the first and second plates 50,50'. The first plate 50 is then raised, leaving the uncoated portion of the product 10 on the top, exposed, and the coated side on the bottom, i.e., within the tablet holder 30 of the plate 50'.

At this point, the preferred embodiment of the method illustrated has completely coated and cured a coating on about one-half of the product 10. It will be understood, however, that the above-described method may be repeated by transferring the plate 50' shown in the lower right section of the illustration to the upper left section, in other words, to the beginning of the process at the point immediately after the individual products 10 have been loaded into the plates 50. In this embodiment of the present invention, the above-described process is repeated and the remainder of the product 10 is coated. It should be further understood, however, that in any event, more or less than one-half of the tablet may be coated to provide different overall coating effects. For instance, if both "passes" coated less than one-half the height of the tablet, a band of uncoated product would remain exposed. On the other hand, if one or both of the "passes" were carried out to a depth substantially greater than one-half the height of the tablet, an overlapped "seam" appearance would be created.

Figure 6:
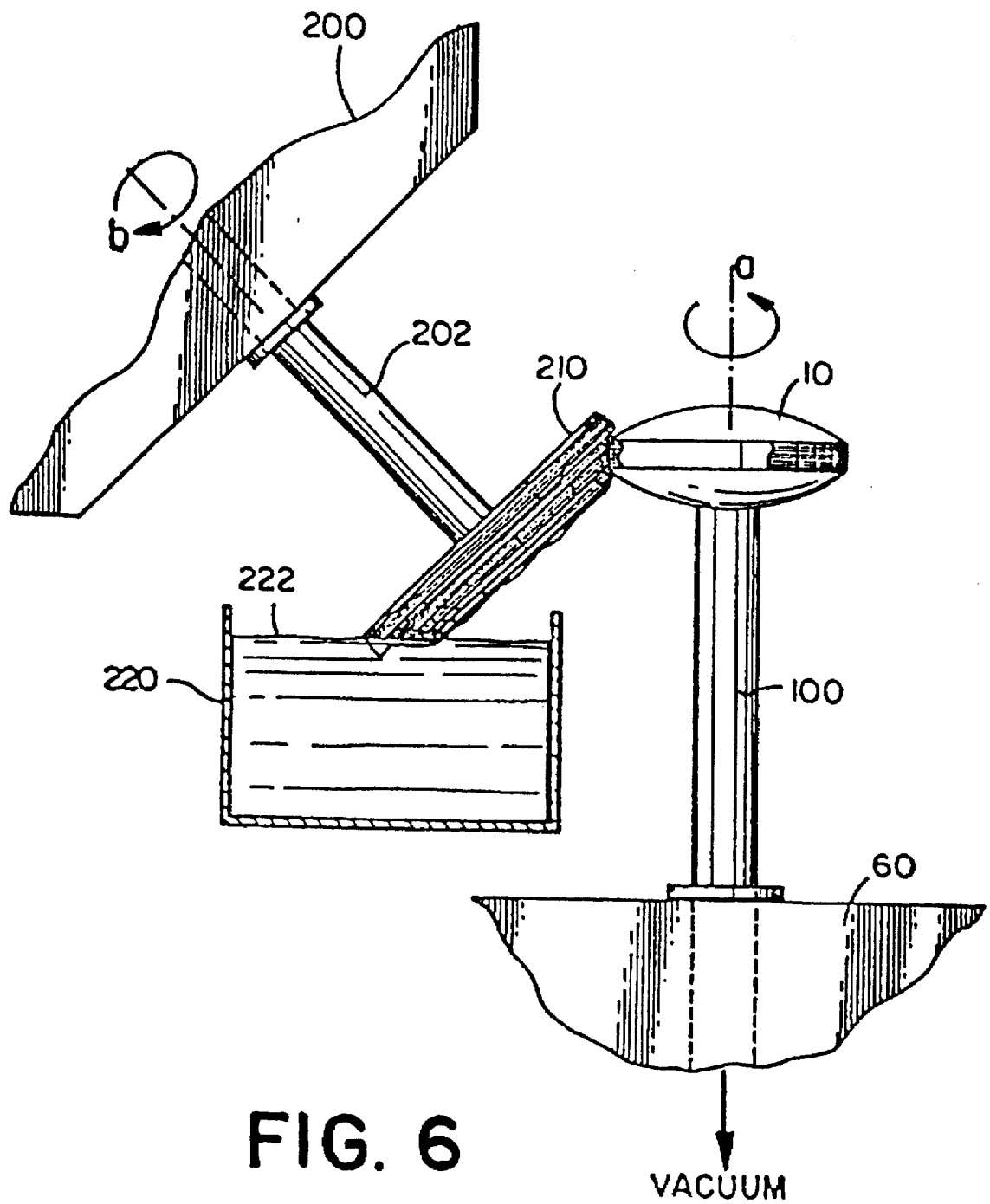
FIG. 6 is a broken away cross-sectional view of a portion of another embodiment of the present invention in which a band of coating material is applied to the products.

Referring now to FIG. 6, another feature of certain embodiments of the present invention is illustrated. In these embodiments, the vacuum tube 100 will be constructed such that it may be rotated about its longitudinal axis as shown by arrow a in FIG. 6. As understood by those of ordinary skill, such rotation may be accomplished using gear trains, belts and pulleys or other means for transferring rotational motion to a shaft. While rotating, the vacuum tube 100 is also acted upon by a source of vacuum, either the vacuum chamber 60 discussed above, or another source. The product 10 is thus firmly held in place upon the rotating vacuum tube 100 as shown. While the product 10 is rotating, it is brought into contact with a rotating wheel 210 or other application means for applying a coating. Preferably, the rotating wheel 210 provided is shaped and manipulated so as to come into close proximity with a portion of the product 10, such as the central "edge" shown. As the wheel 210 and product 10 rotate, the wheel 210 also passes through a quantity of coating material 222 and precisely coats a portion of the product 10. The wheel 210 rotates about a shaft 202 in the direction shown by arrow b and is mounted on a support structure 200 at an appropriate angle.

The present invention therefore also discloses methods whereby a relatively narrow stripe or band of coating material may be applied to a product. Most preferably, the product and the means for applying the coating rotate and are placed in close proximity. The means for applying the coating is preferably at least partially immersed in a quantity of coating material and passes therethrough while rotating. Using the embodiments illustrated in FIG. 6, it is possible not only to provide a different color "band" or stripe, but to also increase the thickness of the coating in a specified section, thereby creating the appearance of a seam or an overlapped gelatin capsule.

Figure 9:
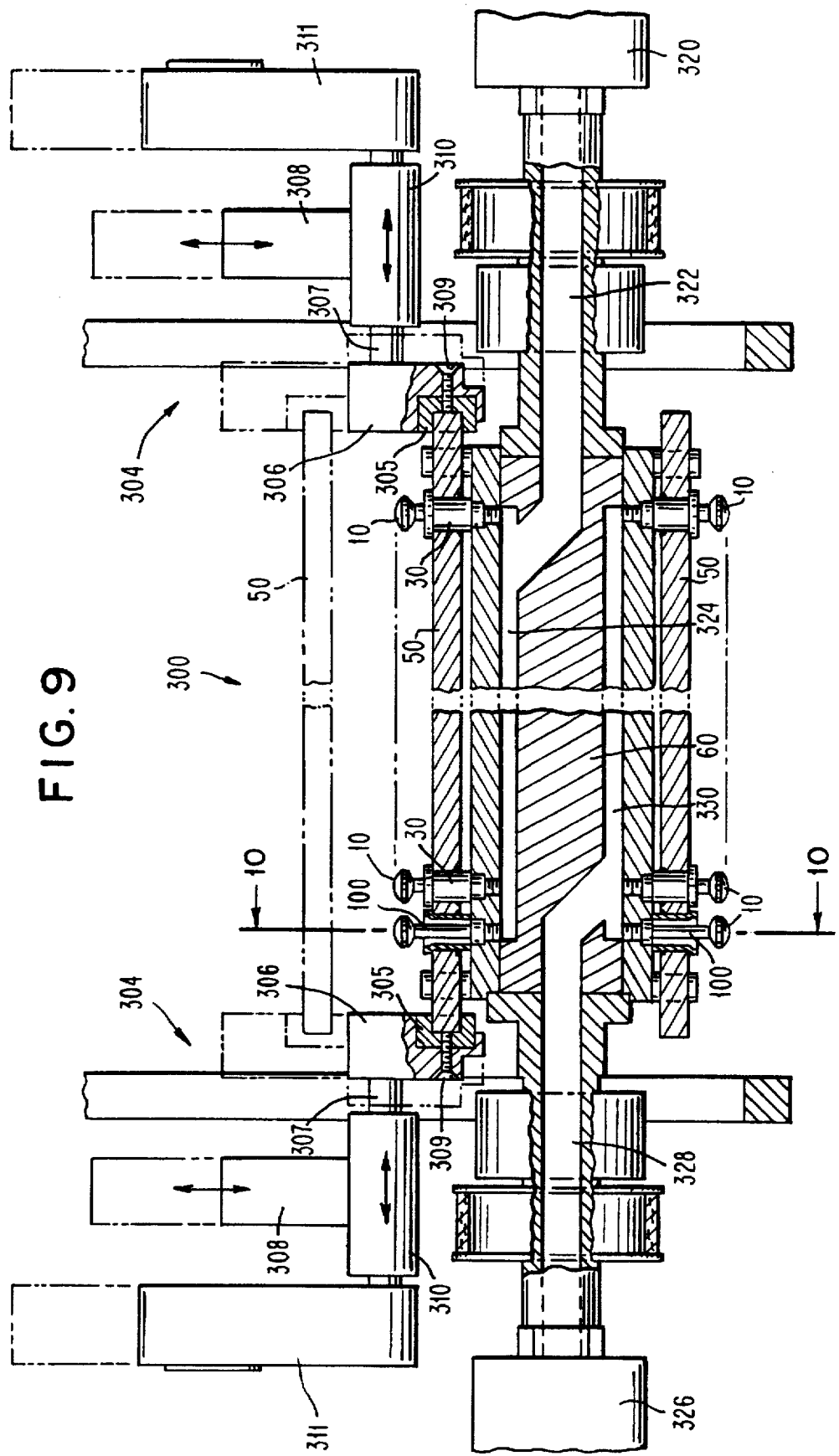
FIG. 9 is a cross-sectional view of the dipping station portion of the apparatus of the present invention.

Referring now to FIG. 9, there is shown a more detailed depiction of a portion of the manipulating means located at a dipping station 300 of the apparatus of the present invention. As noted above, a conveyor or guide means transports the plates 50 from the loading station to the dip station. It is noted here that the plates are advanced by an incremental advancement system through the loading station one row of tablet holders at a time. Upon leaving the loading station, a second advancement device is provided for advancing the plates the width of one plate at a time. Thus, an entire plate is transferred to the dipping station 300 where it is manipulated to coat a portion of the tablets and returned to the guide means to be transferred for further processing.

At the dip station 300 a manipulator means 304 is provided on both sides of the plate 50. The manipulator means 304 takes the plate 50 that has arrived at the dip station 300 and transfers the plate to the vacuum chamber 60. The manipulator means 304 includes a grabber means 306 sized to the exact width of a plate 50. Grabber means 306 is a C-shaped structure designed to engage the side edge and a small portion of the upper and lower edges of plates 50 as the plates are transported from the loading station to the dipping station. The grabber means 306 is coupled to a vertical up and down motion translator means 308 and a horizontal side to side motion translator means 310. Grabber 306 includes a plastic insert 305 which is secured to grabber 306 by set screw 309. The edge of set screw 309 is adjusted to provide a friction fit between the edge of plate 50 and grabber 306. Motion translator 308 is coupled to motion translator 310 such that translator 310 and grabber 306 are moved up and down by translator 308. Any suitable motor driven gear, cam or pully system may be used for motion translators 308 and 310. In FIG. 9, a mechanical cam means 311 actuates translators 308 and 310.

Figure 10:
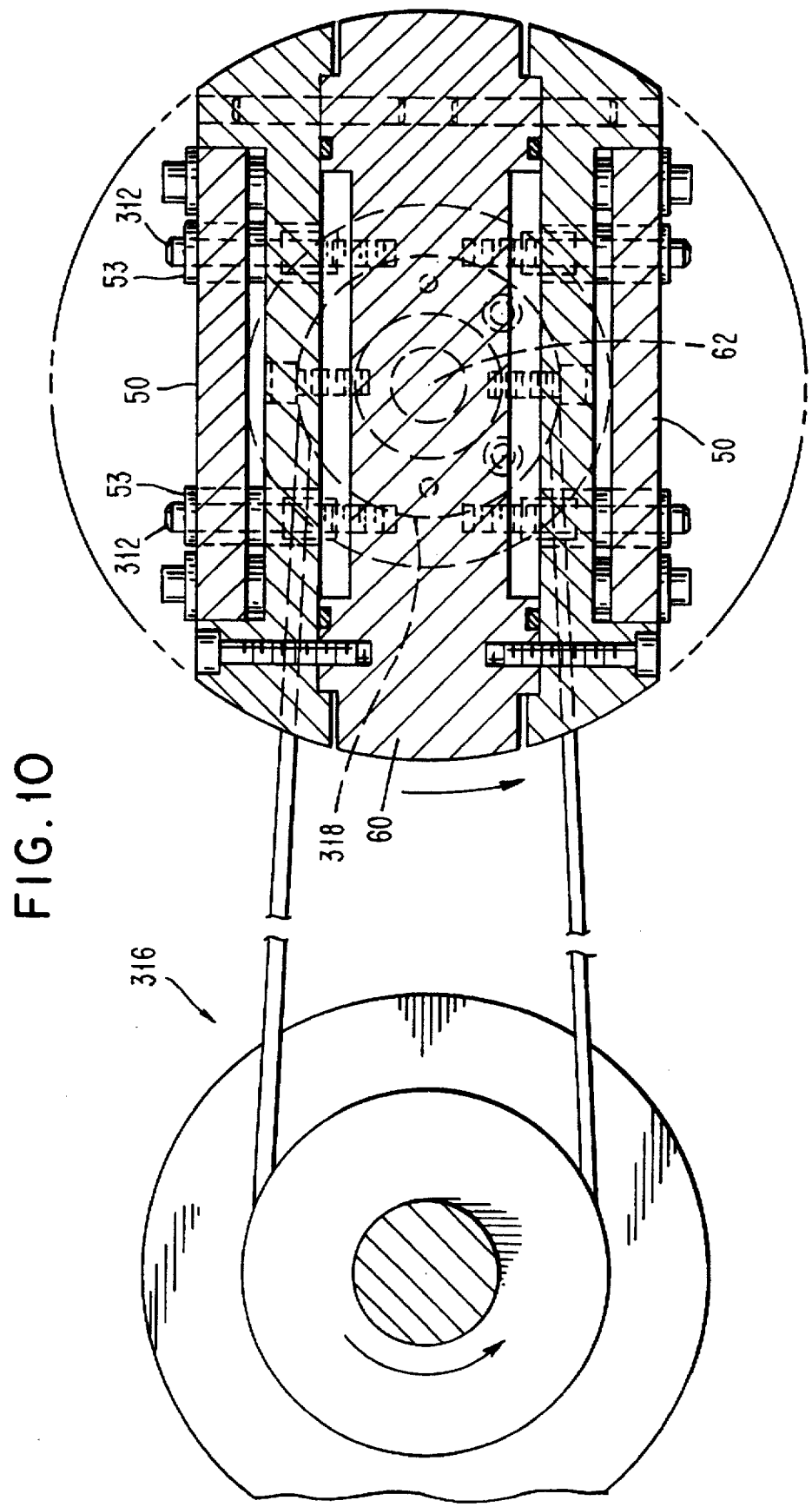
FIG. 10 is a cross-sectional view taken along line 10—10 of FIG. 9.

A plate 50 as it arrives at dipping station 300 is shown in phantom. The plate 50 is shown in solid lines after the manipulation means 304 has mounted the plate 50 onto the vacuum chamber 60. In operation, after the plate 50 has been fully positioned in the dipping station 300, it is engaged by the grabber means 306 on both sides. The relative positions of the grabber means 306 and translator means 308 are shown in phantom. The vertical motion translator means 308 then moves the grabber means 306 and the plate 50 downward to mount the plate 50 onto the vacuum chamber 60. As shown in FIG. 10, the vacuum chamber 60 includes engagement pins 312. The manipulator means 304 transfers the plate 50 onto the vacuum chamber 60 such that the pins 312 enter engagement bushings 53 of plate 50. The engagement pins 312 engage the plate 50 in a friction type fit. The horizontal and vertical translator means 308 and 310 cooperate to transfer the plate 50 while maintaining the plate in a horizontal plane so as not to cause any of the tablets to fall off the plate.

Referring back to FIG. 9, once the grabber means 304 places the plate 50 onto the vacuum chamber 60, the horizontal motion translator means 310 is actuated to move the grabber means 306 outward to disengage the plate 50. The means 310 must move the guide means 306 sufficiently away from the plate 50 to provide clearance to allow the grabber 306 to be returned to its original starting position. The fully retracted position of grabber 306 is shown in phantom. The motion translator means 308 and 310 cooperate to return the grabber 306 to its original position to receive another plate 50.

As noted above, after the plate 50 is mounted to the vacuum chamber 60 the vacuum tubes 100 are raised to extend through the holders 30 to engage and lift a tablet 10 above the holder 30. A vacuum source 320 is then actuated which provides a vacuum through conduit 322 and chamber 324. The vacuum then passes through the tubes 100 and acts to retain the tablet 10 onto the tubes 100 during the rotation of the vacuum chamber 60 and dipping of the tablets 10.

As noted above, the vacuum chamber 60 is adapted to have mounted thereon a pair of plates 50 on opposite sides thereof. In order to mount a second plate 50 onto the vacuum chamber 60, the chamber 60 is rotated 180° or one-half revolution, while the means 304 is returning the grabber means 306 to the guide means. Any conventional rotation means may be employed and in the embodiment of FIG. 10, a common motor driven pulley rotation means 316 is utilized. The rotation means 316 engages a shaft 318 mounted to the vacuum chamber 60 and rotates the vacuum chamber 60 180° around the pivot point 62. After the one-half revolution, the manipulator means 304 by the cooperation of the motion translator means 308 and 310, transfers a second plate 50 from the guide means onto the vacuum chamber 60. After the second plate 50 is deposited onto the vacuum chamber 60, a second set of vacuum tubes are extended through the tablet holders of the second plate. A second vacuum source 326 is actuated to transfer the vacuum through conduit 328 and chamber 330 to the second set of vacuum tubes 100 for retaining the tablets 10 on the second plate 50.

Figure 11:
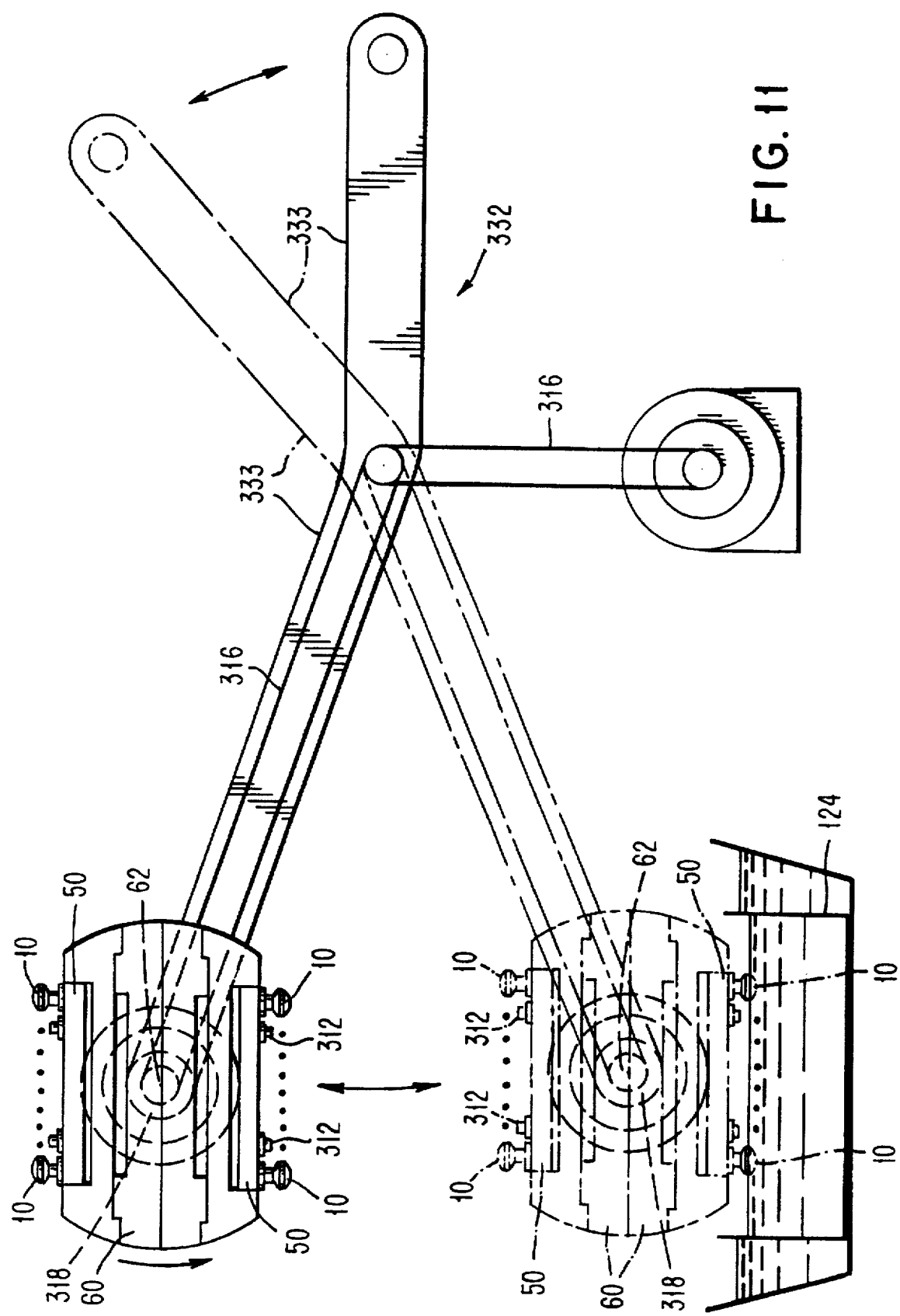
FIG. 11 is a side view of the dipping station.

After the two plates have been loaded onto the vacuum chamber 60, a dipping means raises and lowers the vacuum chamber 60 so that the tablets on one of the plates 50 mounted to the vacuum chamber 60 are at least partially immersed into the coating material in the inner dipping tank 124. As generally shown in FIG. 11, dipping means 332 acts to lower the vacuum chamber 60 toward dipping tank 124 and to raise the vacuum chamber 60 back to its uppermost position. Dipping means 332 may be comprised of a pair of dip arms 333. The position of the plate 50 with tablets immersed into dip tube 124 is shown in phantom in FIG. 11. The dipping means 332 may be driven by any suitable gear, cam or pully system. Preferably, the dipping means 332 and rotation 316 cooperate together as a manipulating means for selectively rotating the vacuum chamber 60 and for lowering and raising the vacuum chamber 60.

In operation, the manipulating means loads the plate 50 into the vacuum chamber 60. The dipping menas 332 lowers the chamber 60 to coat tablets on the first plate. The grabber means 306, after having mounted the second plate 50 onto the vacuum chamber 60, remains in the retracted position while the chamber 60 is being lowered by the dipping means 332. After the tablets 10 on the first plate 50 are dipped, the dipping means 332 returns the vacuum chamber 60 to the rotation position where rotation means 316 rotates the chamber 60 180°. The first plate 50 having partially coated tablets is now aligned with the grabber means 306, which is actuated to reengage the first plate 50 to transfer the plate 50 back to the guide means. The vacuum source is then turned off and the tubes are retracted. The grabber means 306 is also retracted to allow the plate advancement means to move the plate 50 with the dipped tablets out of the dipping station and to introduce a new or third plate 50 into the dipping station. The grabber means 306 then mounts the third plate 50 onto the vacuum chamber 60. Dipper means 332 then lowers the vacuum chamber in order to immerse the tablets on the second plate into the dip tank 124 and raises the vacuum chamber thereafter to the rotation position. Rotation means 316 then rotates the vacuum chamber another one-half revolution and the grabber means 306 transfers the second plate 50 to the guide means. The next or fourth plate is then transferred to the dipping station and the grabber means 306 mounts that plate onto the vacuum chamber 60. The dipping station then operates sequentially as described above to continually dip product into the dip tank 124 and return the product to the guide means for further processing.

Figure 12:
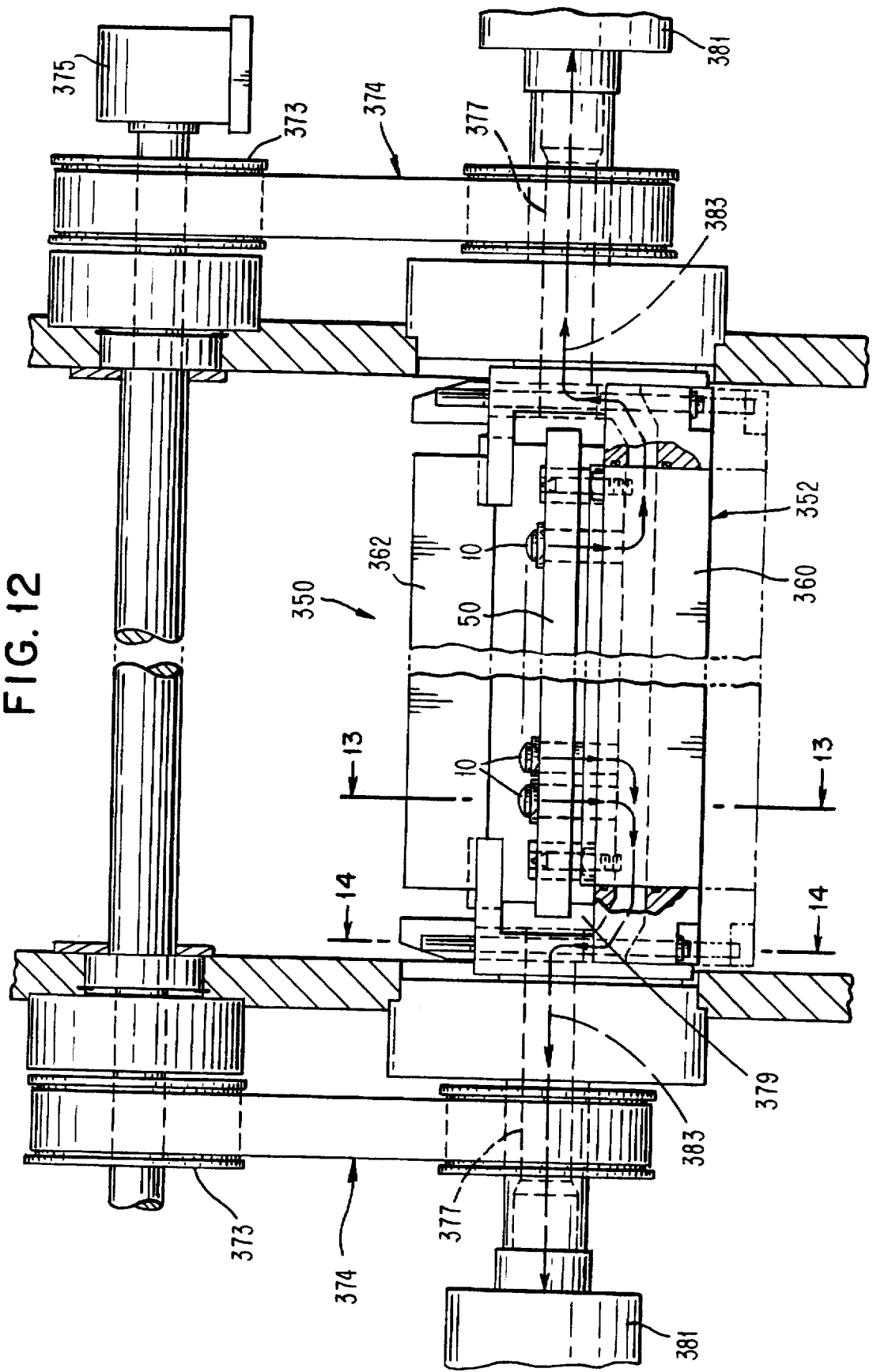
FIG. 12 is a cross-sectional view of the rotating station portion of the apparatus of the present invention.
Figure 13:
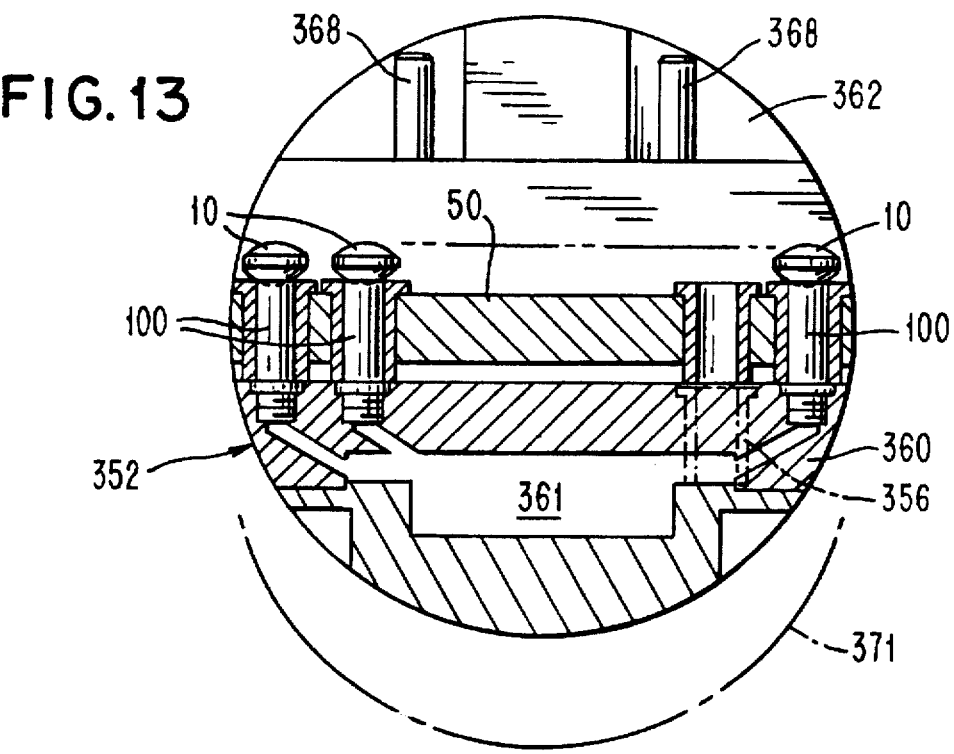
FIG. 13 is a cross-sectional view taken along line 13—13 of FIG. 12.

As noted above, the plate 50 having the product that has just been immersed in the coating material at the dipping station is transferred along the guide means to a rotating station 350 shown in FIG. 12. The rotating station 350 includes a second vacuum chamber means 352. As shown in FIG. 13, the second vacuum chamber means 352 also includes a set of vacuum tubes 100 disposed within the second vacuum chamber that are connected to a vacuum source. When the plate 50 is transported to the rotating station 350, the vacuum tubes 100 are positioned below the plate 50 as shown in phantom at 356. A vacuum tube actuating means raises the vacuum tubes so that the tubes extend through the tablet holders 30. The tubes engage the tablets 10 seated in the holders 30. When the vacuum source is turned on, the vacuum acts upon the tablets 10 holding the tablets in the holders 30 while the chamber is rotated. The chamber 352 is comprised of a lower vacuum chamber housing 360 and an upper cover member 362. The lower housing 360 includes the vacuum tubes 100 and one or more vacuum chambers 361 coupled to vacuum source 381.

Figure 14:
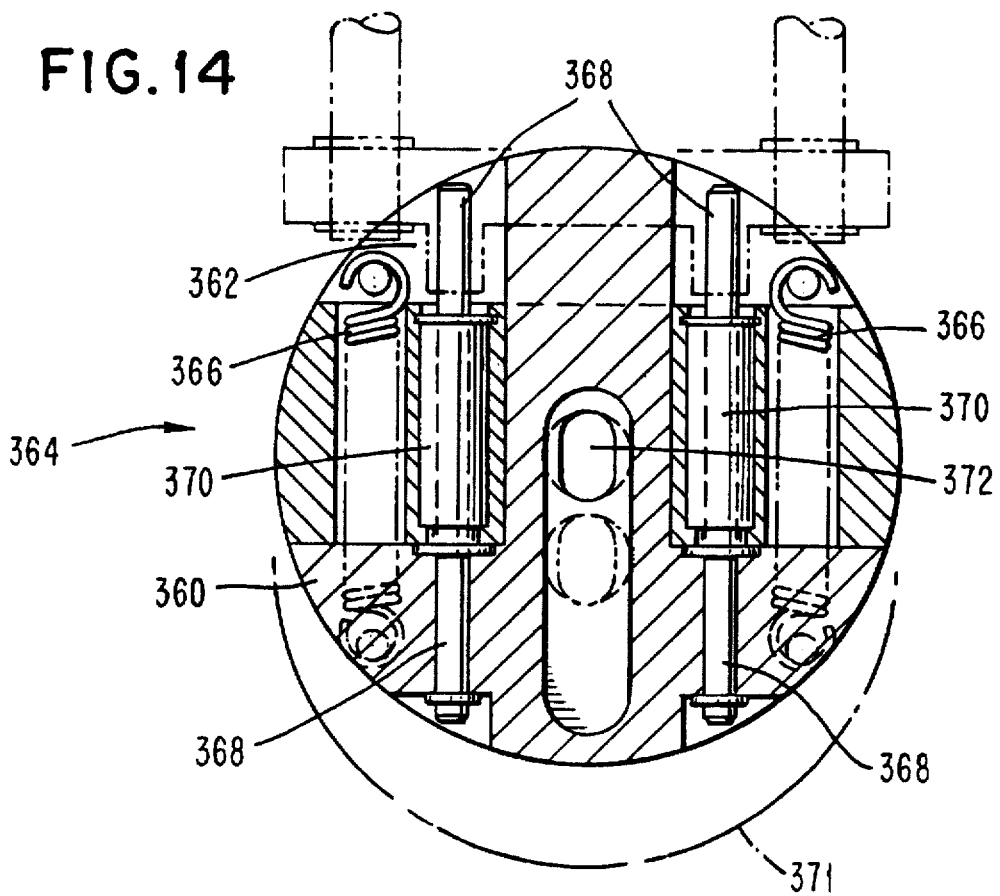
FIG. 14 is a cross-sectional view taken along line 14—14 of FIG. 12.

In the illustrative embodiment shown in FIG. 14, the vacuum tube actuating means is a means for raising and lowering the lower housing 360 relative to the upper member 362. The actuating means also serves to engage the lower housing 360 to the plate 50. As shown in FIG. 14, the actuating means 364 includes a spring means 366 connecting the lower section 360 to the upper section 362. Engagement pins 368 extend from the lower section 360 to the upper section 362 through ball bushings 370. The springs means 366 are positioned to maintain a sufficient space between the upper portion 362 and lower portion 360 for a plate 50 to enter the rotating station and for maintaining the vacuum tubes below the plate 50. A drive means shown in FIG. 15 acts against the spring force to compress the spring and thereby raises the lower portion 360 the predetermined amount to extend the vacuum tubes through the holders 30. FIG. 14 shows the lower housing 360 in the upper position, the lower position being shown in phantom at 371. When drive means is released, the springs cause the lower portion to return to its original position with the vacuum tubes clear of plate 50. Fluid connection 372 connects the vacuum sources 381 (See FIG. 12) to the vacuum chamber. The vacuum sources 381 are activated and a vacuum is created within vacuum chamber 361 along fluid path 383.

Referring back to FIG. 12, after the vacuum tubes are extended into the holders 30, a rotating means 374 which may be a gear, cam or pully operated system, rotates the second vacuum chamber one revolution or 360°. In the example shown in FIG. 12, a motor 375 drives pullies 373 which in turn rotates a shaft 377 which is connected to holding block 379. Block 379 is attached to vacuum chamber means 352 so that rotation of the shaft 377 causes chamber means 352 and plate 50 to be rotated. The rotation of the plate with the coated tablet serves for setting and spreading the gelatin over the portion of the tablet that has been coated.

Figure 15:
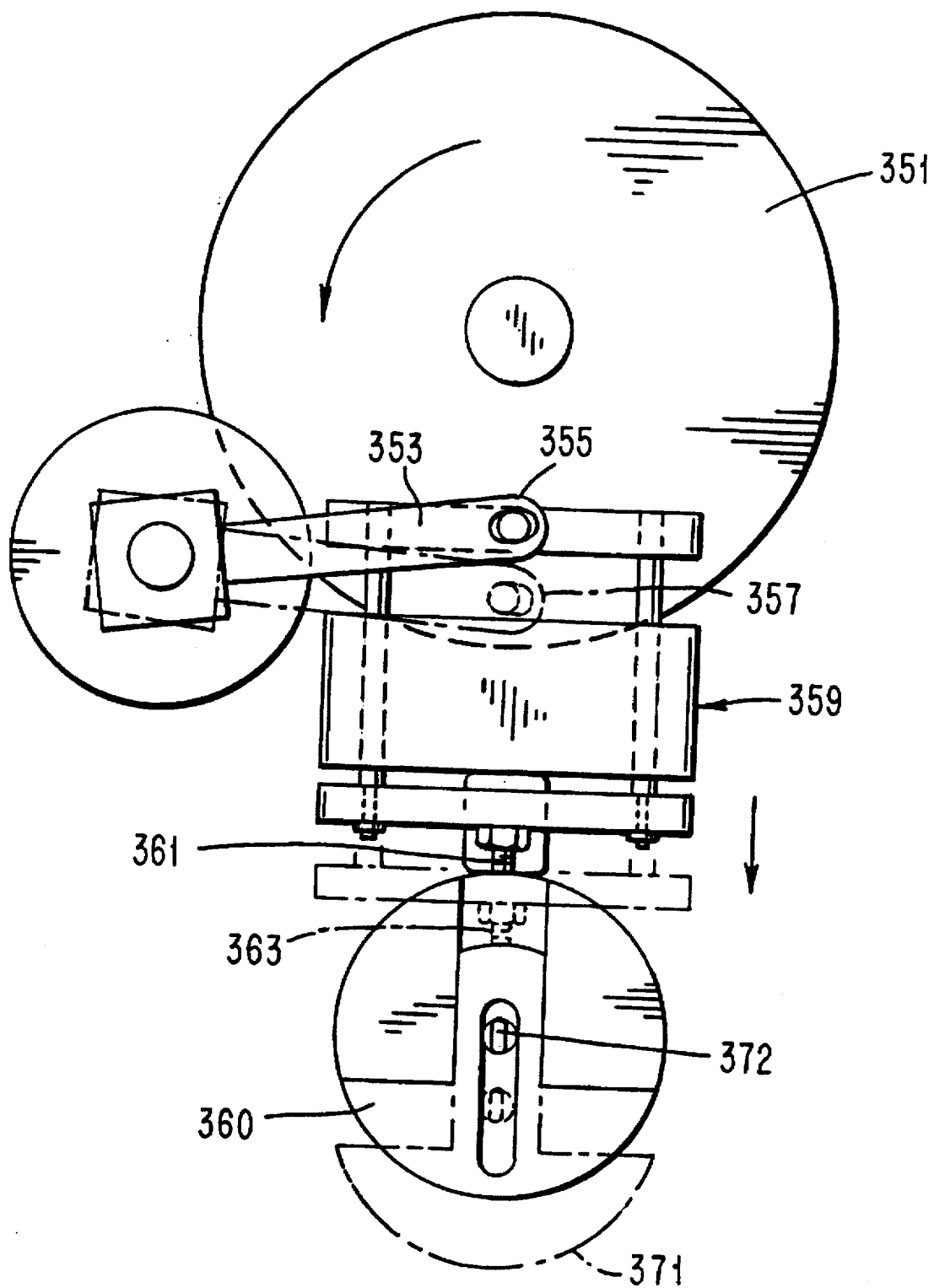
FIG. 15 is a side view of the drive mechanism for raising and lowering the lower portion of the second vacuum chamber means.

FIG. 15 shows the drive mechanism for raising and lowering the lower portion 360 of the second vacuum chamber means 352. A rotating cam plate 351 causes lever arm 353 to reciprocate between the position at 355 and the position shown in phantom at 357. Lever arm 353 is connected to a vertical motion assembly 359 which has abutment surface 361. Surface 361 reciprocates between the up position as shown and the down position shown in phantom at 363. This surface contacts the upper surface of vacuum chamber 360 and moves the chamber to position 371.

After the second vacuum chamber 352 has been rotated one revolution, the drive means disengages the vacuum tubes and the plate 50 is transported to the next processing station. The next plate 50 having coated tablets is then transported into the rotating station. Plates 50 are continually processed in a like manner.

In one preferred embodiment of the present invention, the upper cover member 362 and the lower vacuum chamber housing 360 are each in the shape of a half cylinder each having a flat surface, with the flat surfaces of the upper and lower members facing each other thereby forming a cylindrically shaped second vacuum chamber means 352, which has a circular cross-section. The lower and upper members are adapted to engage and rotate the plates 360° about the longitudinal axis of the plate.

Figure 16:
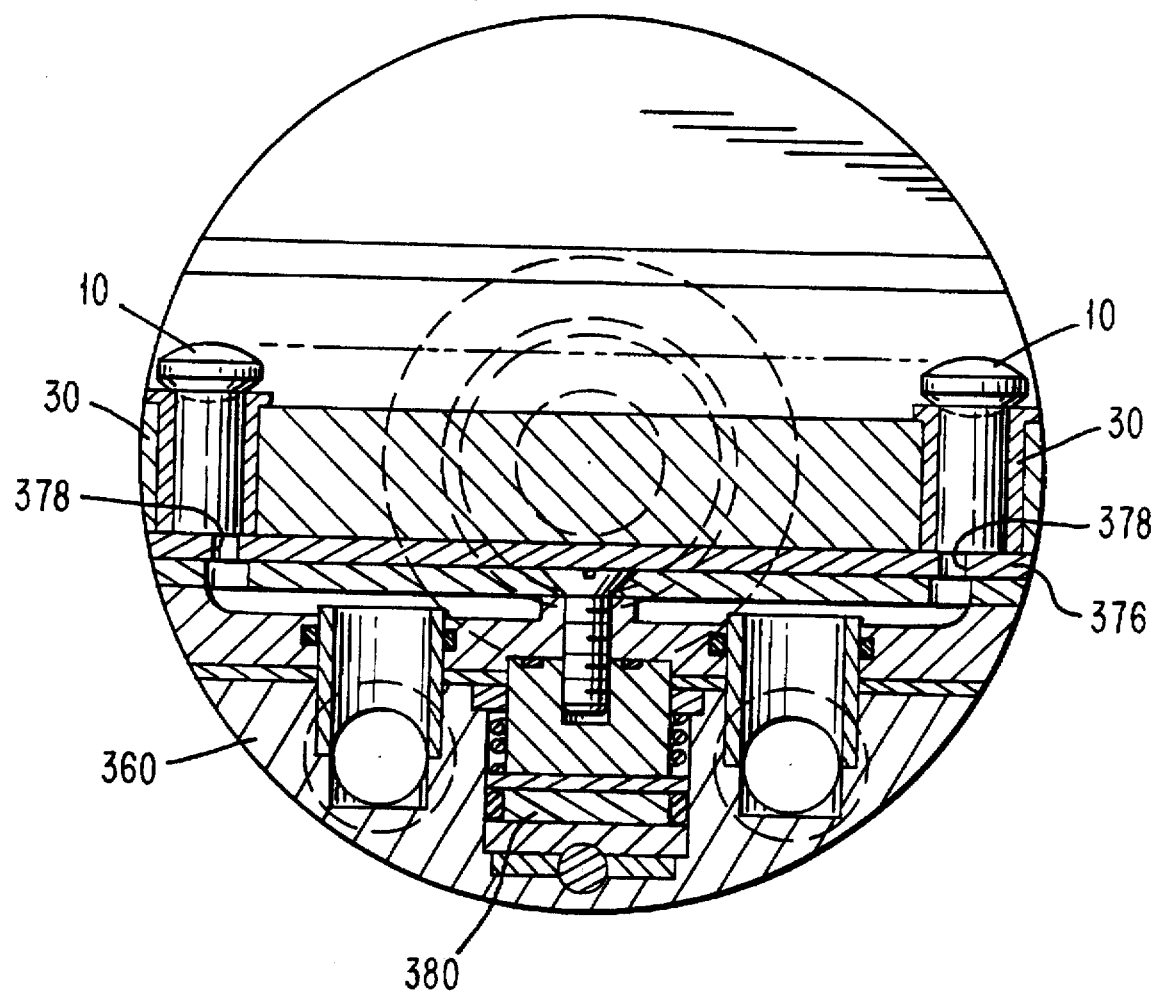
FIG. 16 is a cross-sectional view of an alternative embodiment of a portion of the rotating station of FIG. 12.

In an alternative embodiment of the second vacuum chamber, as shown in FIG. 16, the lower vacuum chamber housing 360 does not include vacuum tubes but is provided with a resilient gasket member 376 having a fluid opening 378 in fluid communication with the vacuum source and central bore of the tablet holders 30. An engagement means 380 which may be a spring actuated mechanism engages the vacuum chamber 352 to the plate 50 in a vacuum tight seal. Similar rotation means are used to rotate the plate one revolution.

Figure 17:
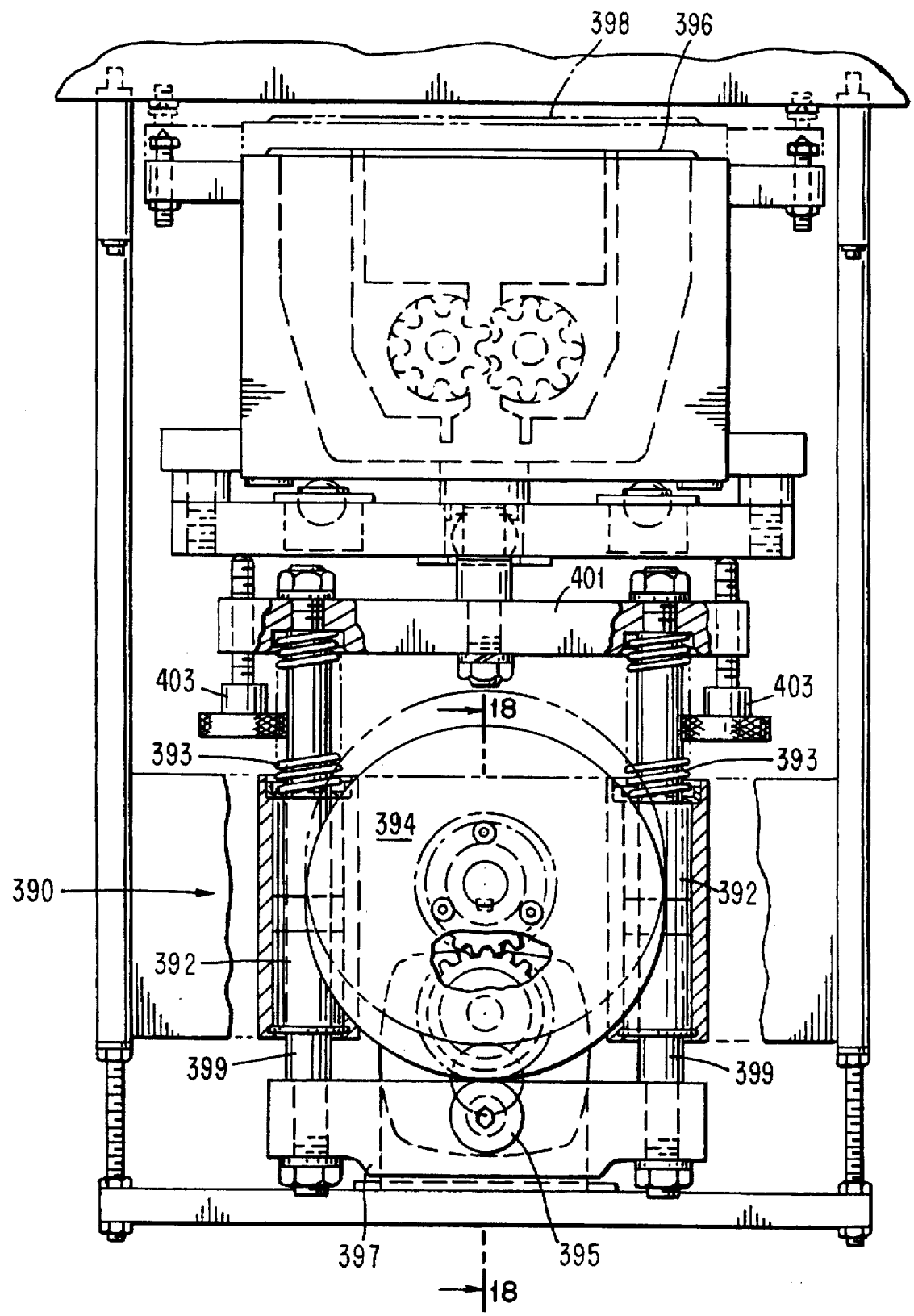
FIG. 17 is an elevational view of a dip pan lifter assembly of the present invention.
Figure 18:
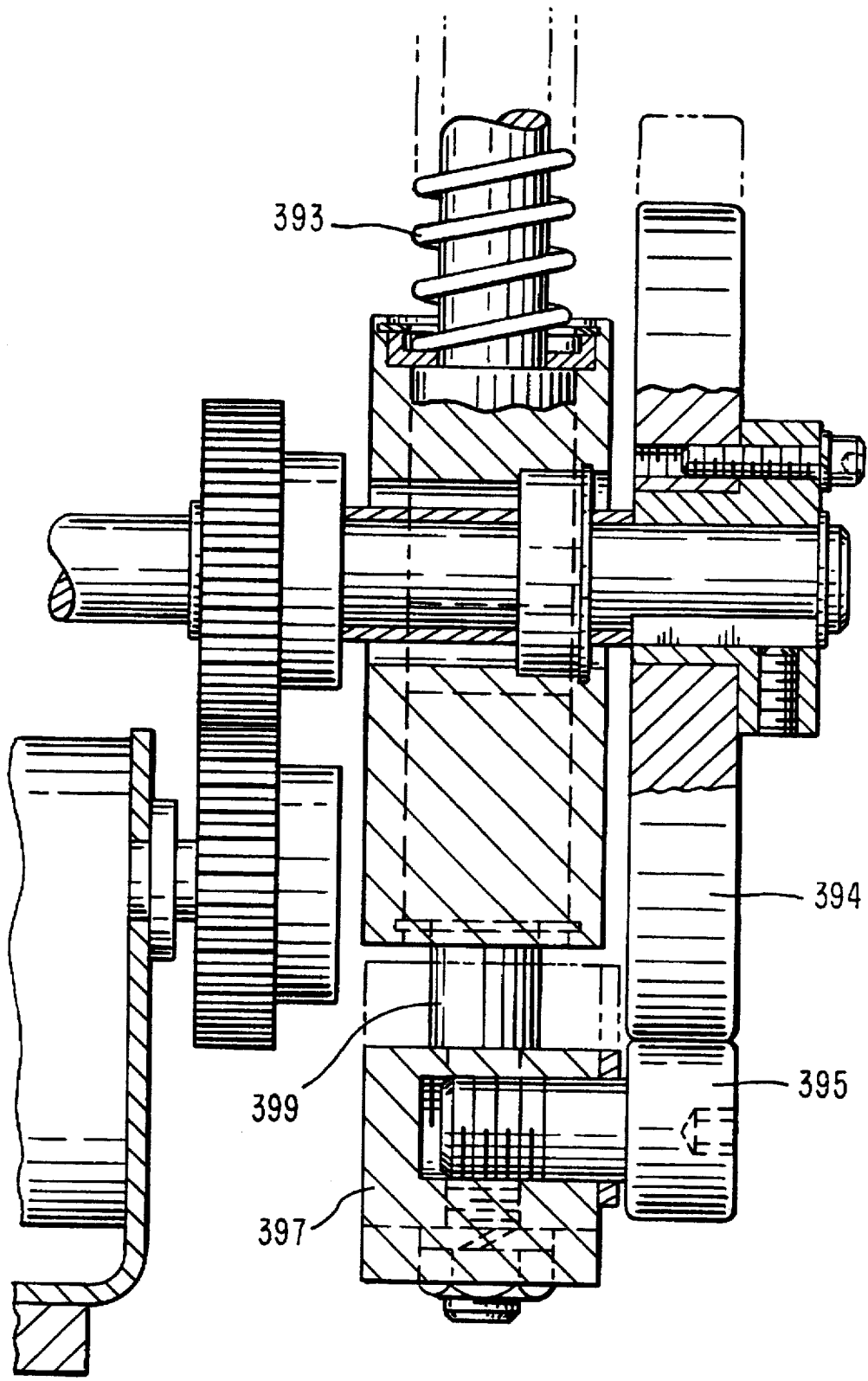
FIG. 18 is a cross-sectional view of a drive mechanism for the assembly of FIG. 17.

Returning now to the dipping station, it has been determined that in the event of a power outage or other undesirable or desirable shut down of the system apparatus, a problem may occur if tablets are immersed in the coating material when the system stops. Tablets that remain in the dip tank for an extended period become unusable because of a build up of the coating material on the tablets. To solve this problem, the present invention includes means for lowering the dip tank in the event of a power outage so that the tablets do not remain in the coating material during the time that the apparatus is not operational. As shown in FIGS. 17 and 18, one embodiment of the dip tank lifter means is provided by a cam actuated spring means 390. The spring means 390 includes ball bushings 392 and springs 393. Rotation of eccentric cam means 394 causes cam follower 395 to move up and down. Cam follower 395 is connected to bar 397 which in turn is attached to rods 399. Rods 399 are bolted to bar 401 which contains tank sealing screw 403. Rods 399 move up and down with ball bushings 392 which moves bar 401 up and down. The two positions of the dip tank are shown with the lower position being shown at 396 and the upper position being shown at 398. The spring operated cam means maintains the dip tank in a normally raised position to allow product to be immersed in the coating material. The actuating means moves the dip tank to a lower position in response to a power cut-off of the apparatus.

While the invention has been particularly shown and described with respect to the preferred embodiments thereof, it should be understood by those skilled in the art that the foregoing and other changes in form and details may be made therein without departing from the spirit and scope of the invention which should be limited only by the scope of the appended claims.

What is claimed is:

1. A method of applying a coating to a product comprising the steps of:

provided a plurality of plate means each having a plurality of product holding means;

placing the product in said product holding means at a loading station;

transporting said plate means form said loading station to a dipping station along a guide means;

mounting at said dipping station a first of said plurality of plate means to a vacuum chamber means having first and second sets of extendible vacuum tubes therein;

extending said first set of vacuum tubes into engagement with the product in said first plate means;

rotating said vacuum chamber one-half revolution about a substantially horizontal axis;

mounting at said dipping station a second of said plurality of plate means to said vacuum chamber means;

extending said second set of vacuum tubes into engagement with the product in said second plate means;

lowering said vacuum chamber means until at least a portion of the product in said first plate means is immersed in a quantity of coating material;

withdrawing said first plate means from said coating material;

rotating said vacuum chamber means one-half revolution about a substantially horizontal axis;

disengaging said first set of vacuum tubes from said product;

transferring said first plate means from said vacuum chamber means to said guide means;

mounting a third of said plurality of plate means to said vacuum chamber means;

extending said first set of vacuum tubes into engagement with said product in said third plate means;

lowering said vacuum chamber until at least a portion of the product in said second plate means is immersed in said coating material;

withdrawing said second plate means from said coating material;

rotating said vacuum chamber one-half revolution about a substantially horizontal axis;

disengaging said second set of vacuum tubes from said product;

transferring said second plate means from said vacuum chamber means to said guide means; and mounting a fourth of said plurality of plate means to said vacuum chamber means.

* * * * *